(12) United States Patent
Angeletakis

(10) Patent No.: US 7,645,443 B2
(45) Date of Patent: Jan. 12, 2010

(54) POLYETHER-BASED COMPOSITION CURABLE BY METATHESIS REACTION

(75) Inventor: Christos Angeletakis, Orange, CA (US)

(73) Assignee: Kerr Corporation, Orange, CA (US)

( * ) Notice: Subject to any disclaimer, the term of this patent is extended or adjusted under 35 U.S.C. 154(b) by 604 days.

(21) Appl. No.: 11/276,270

(22) Filed: Feb. 21, 2006

(65) Prior Publication Data

US 2006/0171900 A1    Aug. 3, 2006

Related U.S. Application Data

(63) Continuation-in-part of application No. 10/988,881, filed on Nov. 15, 2004, now Pat. No. 7,001,590.

(51) Int. Cl.
| | |
|---|---|
| A61K 7/16 | (2006.01) |
| C08L 83/05 | (2006.01) |
| C08L 5/24 | (2006.01) |
| C08L 3/34 | (2006.01) |

(52) U.S. Cl. .................. 424/49; 523/107; 523/109; 524/264; 524/448

(58) Field of Classification Search ........... 525/446; 528/28, 32; 523/109, 107; 424/49; 524/264, 524/448

See application file for complete search history.

(56) References Cited

U.S. PATENT DOCUMENTS

| | | | |
|---|---|---|---|
| 4,584,425 A | 4/1986 | Tom | |
| 4,717,498 A | 1/1988 | Maxon | |
| 4,849,127 A | 7/1989 | Maxon | |
| 5,198,511 A | 3/1993 | Brown-Wensley et al. | |
| 5,266,670 A | 11/1993 | Nakos et al. | |
| 5,296,566 A | 3/1994 | Brown-Wensley et al. | |
| 5,312,881 A | 5/1994 | Marks et al. | |
| 5,330,948 A | 7/1994 | Marks et al. | |
| 5,455,317 A | 10/1995 | Marks et al. | |
| 5,491,206 A | 2/1996 | Brown-Wensley et al. | |
| 5,728,785 A | 3/1998 | Grubbs et al. | |
| 5,831,108 A | 11/1998 | Grubbs et al. | |
| 5,939,504 A | 8/1999 | Woodson, Jr. et al. | |
| 5,942,638 A | 8/1999 | Lichtenhan et al. | |
| 6,001,909 A | 12/1999 | Setiabudi | |
| 6,040,363 A | 3/2000 | Warner et al. | |
| 6,071,459 A | 6/2000 | Warner et al. | |
| 6,075,068 A | 6/2000 | Bissinger | |
| 6,077,805 A | 6/2000 | Van Der Schaaf et al. | |
| 6,121,362 A | 9/2000 | Wanek et al. | |
| 6,252,101 B1 | 6/2001 | Herzig et al. | |
| 6,306,987 B1 | 10/2001 | Van Der Schaaf et al. | |
| 6,310,121 B1 | 10/2001 | Woodson, Jr. et al. | |
| 6,323,295 B1 | 11/2001 | Muehlebach et al. | |
| 6,323,296 B1 | 11/2001 | Warner et al. | |
| 6,403,522 B1 | 6/2002 | Bolm et al. | |
| 6,407,190 B1 | 6/2002 | Van Der Schaaf et al. | |
| 6,409,875 B1 | 6/2002 | Giardello et al. | |
| 6,410,666 B1 | 6/2002 | Grubbs et al. | |
| 6,417,363 B1 | 7/2002 | Van Der Schaaf et al. |
| 6,455,029 B1 | 9/2002 | Angeletakis et al. |
| 6,465,554 B1 | 10/2002 | Van Der Schaaf et al. |
| 6,518,356 B1 | 2/2003 | Friese et al. |
| 6,521,799 B2 | 2/2003 | Wagener et al. |
| 6,525,125 B1 | 2/2003 | Giardello et al. |
| 6,620,955 B1 | 9/2003 | Pederson et al. |
| 6,649,146 B2 | 11/2003 | Angeletakis et al. |
| 6,794,534 B2 | 9/2004 | Grubbs et al. |
| 6,818,586 B2 | 11/2004 | Grubbs et al. |
| 6,921,735 B2 | 7/2005 | Hoveyda et al. |
| 7,001,590 B1 | 2/2006 | Angeletakis |
| 2002/0153096 A1 | 10/2002 | Giardello et al. |
| 2002/0185630 A1 | 12/2002 | Piccinelli et al. |
| 2004/0225073 A1 | 11/2004 | Angeletakis |
| 2005/0159510 A1 | 7/2005 | Smolak et al. |
| 2005/0182218 A1 | 8/2005 | Liaw et al. |

FOREIGN PATENT DOCUMENTS

| | | |
|---|---|---|
| DE | 19859191 A1 | 6/2000 |
| EP | 0796607 A2 | 9/1997 |
| EP | 0771830 A2 | 12/1999 |
| EP | 1025830 A2 | 8/2000 |
| EP | 0940405 A1 | 6/2001 |
| EP | 1241196 A2 | 9/2002 |
| EP | 1555290 A1 | 7/2005 |
| EP | 1656924 A1 | 5/2006 |
| JP | 2001002719 A | 1/2001 |
| JP | 2002284789 A | 10/2002 |
| WO | WO9839346 A1 | 11/1998 |
| WO | WO9900396 A1 | 1/1999 |
| WO | WO9900397 A1 | 1/1999 |
| WO | WO9929701 A1 | 6/1999 |
| WO | WO9950330 A2 | 10/1999 |
| WO | WO9960030 A1 | 11/1999 |
| WO | WO0046255 A1 | 8/2000 |
| WO | WO0232338 A2 | 4/2002 |
| WO | WO03093351 A1 | 11/2003 |

OTHER PUBLICATIONS

European Patent Office, European Search Report, Mar. 13, 2006, 5 pp.

European Patent Office, Search Report and Written Opinion for related EP Patent Application No. 07250732.0, dated Jul. 5, 2007, 6 pgs.

(Continued)

Primary Examiner—Robert D. Harlan
(74) Attorney, Agent, or Firm—Wood, Herron & Evans, LLP

(57) ABSTRACT

One-part and two-part compositions curable by a metathesis reaction comprising a resin containing a polyether-based substrate with at least two cycloolefin groups per molecule curable by a metathesis reaction with a metathesis catalyst. These compositions may optionally contain a reaction control agent for slowing the progress of the metathesis reaction. The metathesis catalyst can be a ruthenium carbene complex catalyst. The substrate may be, for example, a difunctional urethane polyester or polyether carboxylate containing norbornenyl end groups.

20 Claims, No Drawings

OTHER PUBLICATIONS

International Organization for Standardization, Dental elastomeric impression materials; IS0 4823 (1992).

Scholl et al., Synthesis and activity of a new generation of ruthenium-based olefin metathesis catalysts coordinated with 1,3-dimesityl-4,5-dihydroimidazol-2-ylidene ligands, Org. Lett., vol. 1, No. 6, 953-956 (1999).

Chevalier et al., Ring-opening olefin metathesis polymerisation (ROMP) as a potential cross-linking mechanism for siloxane polymers, J. of Inorganic and Organometallic Polymers, vol. 9, No. 3, 151-164 (1999).

L. Lecamp et al., Polydimethyl siloxane photoreticulable par vole cationique-I, Eur. Polym. J., vol. 33, No. 9, 1453-1462 (1997).

Kim et al., Surface-initiated ring-opening metathesis polymerization on Si/SiO2, Macromolecules 2000, 33(8), 2793-2795 (2000).

POLYETHER-BASED COMPOSITION CURABLE BY METATHESIS REACTION

CROSS REFERENCE TO RELATED APPLICATIONS

This application is a continuation-in-part of, commonly-owned application Ser. No. 10/988,881, filed Nov. 15, 2004, now U.S. Pat. No. 7,001,590, the disclosure of which is incorporated herein by reference in its entirety as if completely set forth herein below. This application is also related to co-pending, commonly-owned U.S. patent application Ser. No. 10/430,590 filed May 6, 2003, entitled METHOD OF CURING A COMPOSITION BY METATHESIS REACTION USING REACTION CONTROL AGENT, and to commonly-owned U.S. patent application Ser. No. 11/276,273 filed on even date herewith entitled POLYETHER-BASED DENTAL IMPRESSION MATERIAL CURABLE BY METATHESIS REACTION, the disclosures of which are incorporated herein by reference in their entirety as if completely set forth herein below.

FIELD OF THE INVENTION

This invention relates to polyether-based compositions that undergo a metathesis reaction initiated by a metathesis catalyst. More specifically, the invention relates to ring opening metathesis polymerization (ROMP) of functionalized polyether urethane norbornenecarboxylates catalyzed with metal carbene complexes.

BACKGROUND OF THE INVENTION

Several types of thermoset polymers are generally used in commerce. One type is the acrylic thermoset polymers cured by a free radical addition mechanism. These polymers are cured by heat initiators, such as peroxides, or by photoinitiators, such as alpha diketones. A characteristic of the cured acrylates, however, is large polymerization shrinkage, which is undesirable for many uses. Another undesirable characteristic of acrylates is the formation of an oxygen-inhibited layer on the surface upon curing.

Another type of thermoset polymers is the one based on cationic polymerization of oxirane (epoxy) monomers. These are cured by use of a two-part system or by use of photoinitiators. The disadvantages of oxirane-derived polymers, however, are high water uptake in service, large polymerization shrinkage, and high cost.

Another type of thermoset polymers is the one based on a ring-opening metathesis polymerization (ROMP) mechanism. Metathesis is generally understood to mean the metal catalyzed redistribution of carbon-carbon double bonds. The polymerizable composition comprises a resin system that includes functionalities or groups that are curable by ROMP together with a metathesis catalyst, such as a ruthenium carbene complex. However, to efficiently utilize ROMP to prepare polymers, there is a need to control the progress of polymerization, particularly for molding applications, and especially in one-part systems.

In addition to ROMP, other metathesis reaction systems utilize metathesis catalysts, for example ring closing metathesis, acyclic diene metathesis polymerization, ring opening metathesis and cross metathesis. There is further a need for controlling the progress of reaction in these other metathesis reaction systems.

The thermoset monomer types that are curable by ROMP are the cycloolefins, such as dicyclopentadiene (DCPD), as described in Woodson U.S. Pat. No. 6,310,121. These resins are usually molded, and there is a further need to control the progress of the metathesis reaction for this monomer type.

There is also a need for thermoset polymers that can afford similar physical property profiles as the analogous acrylic, aziridine and oxirane systems, such as hydrophilicity, tailored modulus for the desired application, hardness, etc. with a minimum of their disadvantages, such as polymerization shrinkage.

Various patents address the polymerization of cyclic olefins such as DCPD, tricyclododecene and the like, for example, Tom U.S. Pat. No. 4,584,425. Two of these patents mention compounds containing norbornenyl functional groups and ROMP with the goal of producing a highly crosslinked polymer, namely Bissinger U.S. Pat. No. 6,075,068 and EP 1025830A2 by Moszner. Bissinger describes several ROMP catalyzed resin systems based on dinorbornenyl dicarboxylate ester (DNBDE) compounds or a combination of DNBDE compounds and acrylates. A trinorbornenyl tricarboxylate ester (TNBTE) compound was also disclosed. Moszner describes ROMP of norbornenyl monocarboxylate, which is a monofunctional monomer. However, the combination of the particular resins and catalysts does not achieve the controlled reaction progress desired for many applications.

In dentistry, addition silicones are the most widely used impression materials. Addition silicones cure with a hydrosilation mechanism and contain a platinum compound as a catalyst. Despite the addition of various surfactants, the hydrophilicity of the materials as measured by contact angle measurements, especially before set is completed, is very low. This reduces the ability of the impression material to displace oral fluids during curing and results in a compromised impression. Another class of impression material, the polyethers, as exemplified by IMPREGUM™ (from 3M ESPE) are 2-part systems containing imine terminated polyether copolymers cured by reaction with a strong acid. However, these polyethers suffer from high rigidity, which is a property of crosslinked polyethers, and poor taste and smell due to the presence of imines and strong acids.

There is thus a need for a polyether-based impression material with improved flexibility, taste and smell.

SUMMARY OF THE INVENTION

The present invention provides a one-part composition that upon heating of its components undergoes a metathesis reaction, wherein the one-part composition contains components for controlling and catalyzing the metathesis reaction. The present invention further provides a two-part composition comprising a base part and a catalyst part that upon mixing the parts undergoes a metathesis reaction, and a component for controlling the reaction is optional. The one-part and two-part compositions of the present invention each comprise at least 0.1 wt. % of a substrate containing at least two cycloolefin groups capable of undergoing a metathesis reaction. The substrate has the formula:

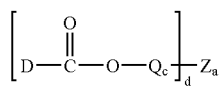

wherein:

$a=1-100$, $c=0$ or $1$ and $d=2-100$,

Q is a linear, branched, cyclic or polycyclic organic residue optionally containing siloxane groups (Si—O—Si) and optionally containing heteroatoms selected from the group consisting of B, N, O, Si, P, and S, Z is a linear, branched, cyclic or polycyclic urethane polyether or urethane polyester optionally containing siloxane groups (Si—O—Si) and optionally containing heteroatoms selected from the group consisting of B, N, O, Si, P, and S, and D is a cycloolefinic residue and is different than Q or Z. By way of example, D may be a cycloolefinic residue selected from norbornenyl, norbornenylethyl, cyclopentenyl, 7-oxanorbomenyl, norbornadienyl, and/or 7-oxanorbornadienyl. In the two-part compositions of the present invention, the substrate is part of the base part.

The one-part compositions of the present invention further comprise a ruthenium or osmium carbene complex catalyst that is capable of initiating a metathesis reaction, such as ring-opening metathesis polymerization (ROMP), and a reaction control agent for slowing the progress of the reaction, the catalyst and reaction control agent mixed with the olefinic substrate. In the two-part compositions of the present invention, the catalyst part contains the catalyst, which upon mixing of the catalyst part with the base part, initiates the metathesis reaction of the olefinic substrate. For the two-part compositions, a reaction control agent is optionally used as a component of the base part. In either the one-part or two-part compositions, the catalyst may have the following structure:

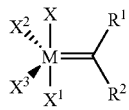

wherein:

M is ruthenium or osmium,

X is an alkylidene ligand with basicity higher than that of tricyclohexylphosphine ($PCy_3$), $X^1$ is either $PCy_3$ or a neutral electron donor ligand with basicity lower than that of $PCy_3$, $X^2$ and $X^3$ are either the same or different and are any anionic ligand, and $R^1$ and $R^2$ are the same or different and are each a linear, branched, cyclic or polycyclic organic residue optionally containing siloxane groups (Si—O—Si) and optionally containing heteroatoms selected from the group consisting of B, N, O, Si, P, and S.

In a two-part composition of the present invention, the catalyst may also have the following structure:

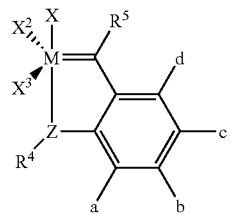

wherein:

M is ruthenium or osmium,

X is an alkylidene ligand with basicity higher than that of tricyclohexylphosphine ($PCy_3$), $X^2$ and $X^3$ are either the same or different and are any anionic ligand, Z is oxygen (O) or sulfur (S), and $R^4$, $R^5$, a, b, c, and d are the same or different and are each a linear, branched, cyclic or polycyclic organic residue optionally containing siloxane groups (Si—O—Si) and optionally containing heteroatoms selected from the group consisting of B, N, O, Si, P, and S.

The reaction control agent present in the one-part compositions and optionally in the two part compositions of the present invention slows the progress of the metathesis reaction. The control agent allows the composition to be cured after a certain delayed time after mixing (work time or pot life) or allows for completion of curing only by heating to temperatures above the mixing temperature. The reaction control agent is an organic compound that contains carbon-carbon double and/or triple bonds and one or more central Group 14 atoms, and can further contain, in the case of a Si central atom, oxygen atoms connected to the silicon to form siloxane bonds. More particularly, the reaction control agent has the following structure:

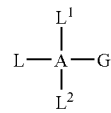

wherein:

G is selected from the group consisting of: $L^3$,

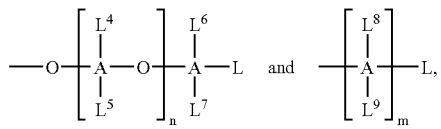

L is a hydrocarbon fragment containing a double or triple bond, $L^1$-$L^9$ are each independently selected from the group consisting of L, alkyl, aryl, aralkyl or haloalkyl, A is a Group 14 atom, n=0-20, and m=0-20.

In an exemplary embodiment, the reaction control agent is tetraallyl silane (TAS). In another exemplary embodiment, the reaction control agent is tetraallyloxy silane (TAOS). In a further exemplary embodiment, the reaction control agent prevents the metathesis reaction from proceeding to completion until an elevated temperature above the mixing temperature is applied to the one-part composition.

DETAILED DESCRIPTION

The present invention provides formulations of ruthenium or osmium carbene complexes together with a base resin that includes a substrate containing at least two cycloolefin groups curable by a metathesis reaction, either as a one-part system or a two-part (catalyst-base) system. The compositions of the present invention may also contain fillers and other additives, such as pigments or surfactants, for performance improvement. As used herein, the term "base" or "base component" refers to the chief component or active ingredient that undergoes the metathesis reaction, which in the present invention is the substrate containing at least two cycloolefin groups. A "base resin" is a resin that contains that chief component. The term "base part" refers to the part in a part-part (two-part) composition that contains the chief component, while the other part, the catalyst part, contains the catalyst that initiates the metathesis reaction of that chief component upon mixing of the two parts.

When cured as a one-part system, the composition of the present invention additionally contains a reaction control agent that allows control of the progress of the metathesis reaction. In this embodiment, the metathesis catalyst and the reaction control agent are pre-dissolved in a suitable fluid, such as a phenylated silicone fluid, and mixed with the base component, which includes at least 0.1 wt. % of a resin having at least two cycloolefin groups, such as cycloalkenyl groups, per molecule. For example, the base resin may include a carboxylate ester backbone functionalized with at least two cycloolefin groups. In another example, the base resin may be a difunctional or trifunctional carboxylate ester containing norbornenyl end groups. In yet another example, the base resin may be a difunctional urethane polyether carboxylate containing norbornenyl end groups. The base component may further include monofunctional resins, such as a monofunctional carboxylate ester containing a norbornenyl end group. The compositions of this embodiment undergo a metathesis reaction initiated by the metathesis catalyst. The difunctional and polyfunctional resins, even in very small amounts, have a marked effect on the degree of crosslinking in the compositions of the present invention when activated by the particular metathesis catalysts disclosed herein. The reaction control agent, such as Tetraallyloxysilane (TAOS), controls the progress of the reaction to increase the working time of the composition and to control the viscosity build up. Depending on the nature of the control agent, completion of the reaction may be prevented until the composition is exposed to temperatures higher than the mixing temperature. Thus, the present invention provides formulations of ruthenium carbene complexes together with reaction control agents that allow control of the progress of a metathesis reaction on a substrate having at least two cycloolefin groups.

When cured as a two-part (base-catalyst) system, the composition of the present invention may optionally include a reaction control agent in the base part. In this embodiment, the metathesis catalyst is pre-dissolved in a suitable fluid, such as a phenylated silicone fluid, to form a catalyst part. The base part contains a resin having at least two cycloolefin groups, such as cycloalkenyl groups, per molecule. For example, the base resin may include a carboxylate ester backbone functionalized with at least two cycloolefin groups. In another example, the base resin may be a bifunctional or trifunctional carboxylate ester containing norbornenyl end groups. In yet another example, the base resin may be a difunctional urethane polyether carboxylate containing norbornenyl end groups. The base part also may optionally contain a reaction control agent to adjust the work/set time to a desirable level. Upon mixing the two parts together, the composition of this embodiment undergoes a metathesis reaction initiated by the metathesis catalyst. In an exemplary embodiment, the metathesis reaction proceeds to completion at room temperature. In another exemplary embodiment, the metathesis reaction proceeds to near completion at room temperature, and a higher temperature is applied to complete the reaction, i.e., to more fully polymerize the mixture.

In both the one-part and two-part formulations of the present invention, the base resin contains a substrate (compound or mixture of compounds) having at least two cycloalkenyl groups that undergo a metathesis reaction, such as ROMP, when mixed with the ruthenium carbine complex. The two functional cycloalkenyl groups, for example, can be norbornenyl or norbornenylethyl groups. By way of further example, the groups may be cyclopentenyl, 7-oxanorbornenyl, norbornadienyl, and/or 7-oxanorbornadienyl.

In one embodiment of the present invention, the substrate has the formula:

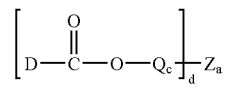

wherein:
a=1-100, c=0 or 1 and d=2-100,

Q is a linear, branched, cyclic or polycyclic organic residue optionally containing siloxane groups (Si—O—Si) and optionally containing heteroatoms selected from the group consisting of B, N, O, Si, P, and S, Z is a linear, branched, cyclic or polycyclic urethane polyether or urethane polyester optionally containing siloxane groups (Si—O—Si) and optionally containing heteroatoms selected from the group consisting of B, N, O, Si, P, and S, and D is a cycloolefinic residue and is different than Q or Z. By way of example, D may be a cycloolefinic residue selected from norbornenyl, norbornenylethyl, cyclopentenyl, 7-oxanorbornenyl, norbornadienyl, and/or 7-oxanorbornadienyl.

A DNBDE may be synthesized via an esterification reaction. As an example, CPD can be reacted with the adduct of hydroxyethyl acrylate with succinic anhydride to give a norbornenyl functional carboxylic acid A. This is followed by esterification of A with polyethylene glycol 400 (PEG 400) using p-toluenesulfonic acid as a catalyst in cyclohexane with azeotropic removal of water to produce Compound 1g as shown in the scheme below.

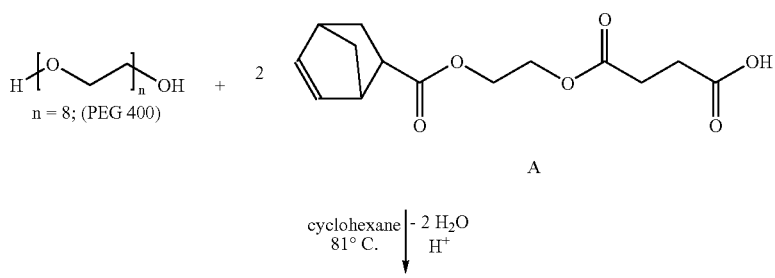

-continued

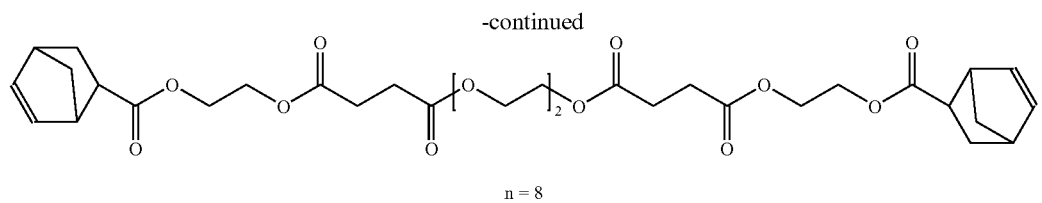

n = 8

Other diols besides PEG 400 can be used, for example polyethylene glycol-polypropylene glycol copolymers such as Pluracol 1062 from BASF. Polyester diols can be used also, for example, ethylene butylene adipic acid polyester diol such as Desmophen 2000KS from Bayer, diethylene glycol adipic acid polyester diol, and the like. As yet another method, the DNBDE can be made via a transesterification reaction using 5-norbornene-2-carboxylic acid methyl ester and a tin catalyst, as an example; acid or base catalysts can also be used. When Z is a polyether fragment or a polyester fragment, the resultant polymer after ROMP can be soft and flexible, which makes it desirable for use as a dental impression material.

However, esterification reactions may not be efficient with relatively high molecular weight polyols, for example, in the analogous situation of the acrylate esters, which are generally not available with polyethylene glycol backbones above 1000 daltons. Acrylate endcapped oligomers, however, are readily available with urethane functionalities via reaction of polyols with isocyanates followed by endcapping with a hydroxyl functional acrylate, such as for example hydroxypropyl acrylate. Analogously norbornenyl group terminated urethane oligomers can be prepared by substituting a hydroxyl functional norbornenylcarboxylate to be used as the endcapper for the hydroxyl functional acrylate. The general structure is shown below:

where E=the endcapper, R=a diisocyanate fragment, and PE=a polyol. In accordance with the present invention then, urethane polyether and polyester oligomers endcapped with norbornenyl groups can thus be prepared for curing using ROMP.

As a first step, an excess of a diisocyanate such as hexane diisocyanate (HDI) was reacted with a polyether diol using a tin catalyst followed by reaction with an endcapper, specifically hydroxypropyl norbornenecarboxylate (HPNBC, E-H in the Scheme below). This endcapper HPNBC was prepared by the reaction of hydroxypropyl acrylate with cyclopentadiene, according to the method discussed in U.S. Pat. No. 7,001,590, incorporated by reference herein. The reaction is shown as follows:

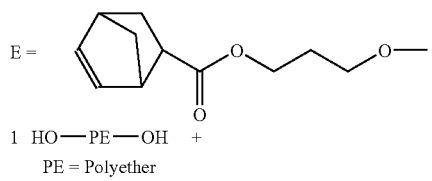

1 HO—PE—OH +
PE = Polyether

-continued

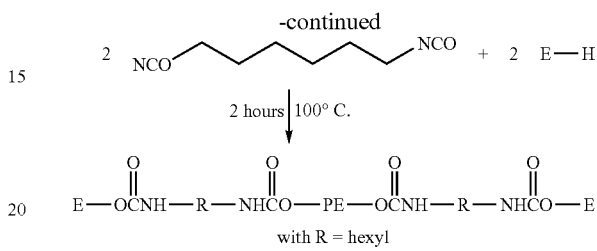

with R = hexyl

The resultant compounds are urethane polyether (UPE) norbornenecarboxylates (terminated with norbornenyl groups). The functional group Z is an adduct of a difunctional polyol with an excess of HDI to afford an isocyanate terminated oligomer. This oligomer reacts with HPNBC to afford a ROMP curable prepolymer.

The two-part compositions of the present invention contemplate a catalyst part and base part that upon mixture with one another, form a curable part/part system in which the metathesis reaction proceeds. Generally, in this system, the catalyst part comprises the metathesis catalyst for initiating polymerization, and a solvent for the catalyst that is miscible or dispersible with the base part and that does not interfere with the metathesis reaction. In the one-part systems, the catalyst is first dissolved in this solvent and then combined with the base component optionally containing the reaction control agent. The solvent may be a siloxane substituted with alkyl groups and arylalkyl or aryl groups. The presence of the aryl or aralkyl groups assist the solubility of the metal carbene complex catalyst while having a relative reduced polarity as compared to a carboxylic ester, such as diethyl phthalate for example. This siloxane can be, for example, 3-phenyl-heptamethyl-trisiloxane. This siloxane can also be a phenyl trimethicone, such as Dow Corning fluid 556 or Silcare 15M30 from Clariant (Sulzbach, Germany). Alternatively, an alkylmethylsiloxane-arylalkylmethylsiloxane copolymer can be used, such as 45-55% hexylmethylsiloxane-(45-55% 2-phenylpropylmethylsiloxane) copolymer. Mixtures of the above, especially for achieving a desired viscosity, can also be employed. Citric acid esters can also be used, for example, CITROFLEX® A4 from Morflex, Inc. The base part generally comprises the substrate that is curable via ROMP or other metathesis reaction and optionally a reaction control agent to control the working time. The composition may further include filler systems and/or optional additives suitable for the particular application, such as pigments or surfactants, which do not interfere with the reaction.

The catalysts useful in the present invention include ruthenium or osmium carbene complexes that are derivatives of the parent benzylidene ruthenium complex 1, known as the Grubbs catalyst, which has the following structure:

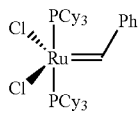

wherein Ph is phenyl, and Cy is cyclohexyl. The ring-opening metathesis activity, working time and/or air stability of the parent complex 1 can be increased by making substitutions to the parent complex 1. Thus, the catalyst used in the present invention may have the following general structure:

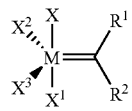

wherein:

M is ruthenium or osmium,

X is an alkylidene ligand with basicity higher than that of tricyclohexylphosphine ($PCy_3$), $X^1$ is either $PCy_3$ or a neutral electron donor ligand with basicity lower than that of $PCy_3$, $X^2$ and $X^3$ are either the same or different and are any anionic ligand, and $R^1$ and $R^2$ are the same or different and are each a linear, branched, cyclic or polycyclic organic residue optionally containing siloxane groups (Si—O—Si) and optionally containing heteroatoms selected from the group consisting of B, N, O, Si, P, and S.

In one category of derivative complexes of the above general structure, referred to generally as complex 2 catalysts, and which are useful as catalysts in the one or two-part compositions of the present invention, X is an alkylidene ligand with basicity higher than that of tricyclohexylphosphine ($PCy_3$) and $X^1$ is $PCy_3$. In one embodiment, for example, a derivative ruthenium complex 2-1 of complex 1 is formed by substituting an alkylidene ligand X, such as a saturated imidazolidine ligand, for one of the tricyclohexylphosphine ($PCy_3$) ligands, in accordance with the following formula:

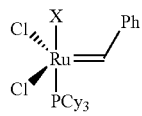

The ligands X may be 4,5-dihydroimidazol-2-ylidenes, which have the following general structure:

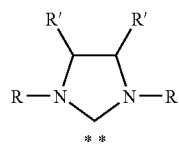

These substituted alkylidene ligands X have a basicity or proton affinity higher than that of tricyclohexylphosphine, which is believed to contribute to the higher activity and higher air stability.

A derivative ruthenium complex 2-2 of complex 1 containing the alkylidene 1,3-bis(2,4,6-trimethylphenyl)-imidazol-2-ylidene (sIMES) ligand is shown here:

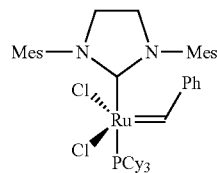

wherein Mes is mesityl (2,4,6 trimethylphenyl). It may be appreciated that the ligand X in structure 2-2, may also be shown with an arc between the N atoms in the imidazolidene group to indicate that a double bond is present therebetween. For example, an alternative equivalent structure for Complex 2-2 is:

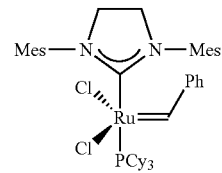

The ligand has been shown both ways in the art of metathesis catalysts, such that the two structures should be considered equivalent and both structures should be understood to represent a double bond between the N atoms in the imidazolidene group. These derivatives of complex 1 are particularly useful in the two-part compositions of the present invention.

In another category of derivative complexes of the general structure, referred to generally as complex 4 catalysts, and which are useful as catalysts in the one or two-part compositions of the present invention, X is an alkylidene ligand with basicity higher than that of tricyclohexylphosphine ($PCy_3$) and $X^1$ is a neutral electron donor ligand with basicity lower than that of $PCy_3$. To achieve a longer working time (pot life) and improve compatibility with the reaction control agents used in the one-part compositions of the present invention, as described further below, the derivative complexes 2 are thus further modified for use in the one-part compositions by substituting the other tricyclohexylphosphine ($PCy_3$) with a neutral electron donor ligand $X^1$ with a lower basicity (as expressed by the pKa) or proton affinity than $PCy_3$. For example, Complex 2-1 is modified to form Complex 4-1 as shown below:

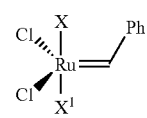

Examples of compound types that can be used as neutral electron donor ligands are: phosphines, phosphites, phosphinites or phosphonites. In an exemplary embodiment, $X^1$ is a phosphine of the formula $PR^3R^4R^5$ where $R^3$, $R^4$, and $R^5$ are alkyl, aralkyl or aryl, with basicity lower than that of $PCy_3$. In a further exemplary embodiment, $R^3$, $R^4$, and $R^5$ are each n-butyl, such that $X^1$ is tri-n-butylphosphine ($PBu_3$), and X is sIMES as shown below as structure 4-2:

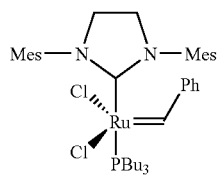

4-2

In another category of derivative complexes of the general structure, referred to generally as complex 3 catalysts, and which are particularly useful in the two-part compositions of the present invention, X is an alkylidene ligand with basicity higher than that of tricyclohexylphosphine ($PCy_3$) and $X^1$, $R^1$ and $R^2$ are substituted, as shown in the following general structure:

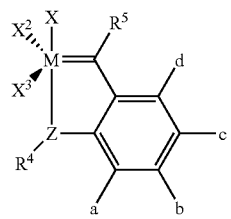

3 wherein:

M is ruthenium or osmium,

X is an alkylidene ligand with basicity higher than that of tricyclohexylphosphine ($PCy_3$), Z is oxygen (O) or sulfur (S)

$X^2$ and $X^3$ are either the same or different and are any anionic ligand, and $R^4$, $R^5$, a, b, c, and d are the same or different and are each a linear, branched, cyclic or polycyclic organic residue optionally containing siloxane groups (Si—O—Si) and optionally containing heteroatoms selected from the group consisting of B, N, O, Si, P, and S.

In an exemplary embodiment of a complex 3 catalyst, M is ruthenium, X is an alkylidene ligand with basicity higher than that of tricyclohexylphosphine ($PCy_3$), $X^2$ and $X^3$ are halogen atoms, Z is oxygen, $R^4$ is a $C_1$ to $C_{10}$ alkyl fragment, a, b, c and d are either hydrogen or a $C_1$ to $C_{10}$ alkyl or a $C_1$ to $C_{10}$ alkoxy group, and $R^5$ is hydrogen.

In another exemplary embodiment of a complex 3 catalyst, M is ruthenium, X is 1,3-bis(2,4,6-trimethylphenyl)-imidazol-2-ylidene (sIMES), $X^2$ and $X^3$ are chlorine atoms, Z is oxygen, $R^4$ is 2-propyl, a, b, c and d are either hydrogen or methoxy, and $R^5$ is hydrogen. Complex 3-1 is an example of this type of exemplary catalyst for a two-part composition of the present invention. Complex 3-1 is 1,3-bis-(2,4,6-trimethylphenyl)-2-(imidazolidinylidene) dichloro(o-isopropoxyphenylmethylene) ruthenium having the following structure:

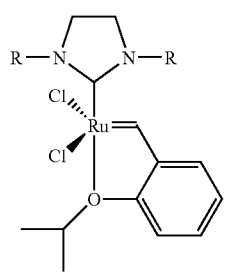

3-1 wherein R is mesityl. Again, the structure may also be shown with an arc between the N atoms in the imidazolidene group to indicate that a double bond is present therebetween, as discussed above. The combination of an olefinic resin system and complex 3-1 is believed to provide a highly efficient metathesis reaction system. Other examples for this category of catalysts, as well as the synthesis of these catalysts, are fully described in U.S. Pat. No. 6,921,735, which is incorporated by reference herein in its entirety.

The one-part compositions of the present invention further comprise a reaction control agent. After mixing of the composition components, the control agent slows the metathesis reaction, and thereby allows for an increase in the time period before cure, or before the metathesis reaction proceeds to completion or to a desired extent short of completion. The length of this time period, also called work time or pot life, may be further controlled by preventing completion of the reaction until the composition is heated to a temperature higher than the mixing temperature, for example, at least 30° C. above the mixing temperature. By way of example, the composition components may be mixed at ambient temperature, followed by heat curing at 60° C. or greater, such as 100° C. or 150° C., or the composition components may be mixed at sub-ambient temperatures (at least 30° C. below ambient), followed by raising the temperature to ambient to complete the reaction. The reaction control agent also allows for control of the viscosity build up as the metathesis reaction proceeds, which is useful for many molding applications.

The reaction control agent is an organic compound that contains carbon-carbon double and/or triple bonds and one or more central Group 14 atoms, and can further contain, in the case of silicon as the central atom(s), oxygen atoms connected to silicon to form siloxane bonds. The reaction control agent has the structure shown below:

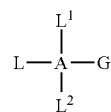

wherein:

G is selected from the group consisting of: $L^3$,

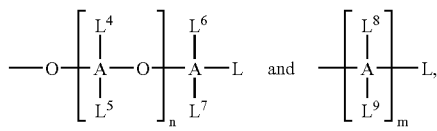

L is a hydrocarbon fragment containing a double or triple bond;

$L^1$-$L^9$ are each independently selected from the group consisting of L, alkyl, aryl, aralkyl or haloalkyl;

A is a Group 14 atom;

n=0-20; and m=0-20.

Of the Group 14 atoms, which include C, Si, Ge, Sn and Pb, the central atom is advantageously Si, Ge or Sn, and more advantageously Si.

In one embodiment of the present invention, G=$L_3$ such that the reaction control agent is a tetracoordinated compound having at least one substituent group L that is a hydrocarbon fragment containing a double or triple bond. Allyl and vinyl groups are hydrocarbon fragments containing a double bond, for example, and alkynyl groups, such as propargyl and ethynyl groups, are hydrocarbon fragments containing a triple bond, for example. For the other substituent groups $L^1$, $L^2$, $L^3$, if not a hydrocarbon fragment containing a double or triple bond, then the substituent group is an alkyl, aryl, aralkyl or haloalkyl group, which are essentially inert to the metathesis reaction. Thus, it is the hydrocarbon fragment containing the double or triple bond that determines the extent of the retardation of the metathesis reaction, such that a greater number of such hydrocarbon fragments would be expected to achieve longer working times than similar structures containing fewer of such hydrocarbon fragments. An exemplary inert substituent is the methyl group.

In the embodiment of the present invention where G is defined as:

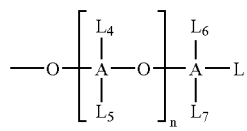

the central atom A is Si, such that the reaction control agent contains a straight chain siloxane compound in which the ends of the chain are capped by hydrocarbon fragments containing a double or triple bond. The substituent groups within the chain (i.e., $L^1$, $L^2$, $L^4$, $L^5$, $L^6$, $L^7$) may also be hydrocarbon fragments containing double or triple bonds or may be an inert substituent including alkyl, aryl, aralkyl or haloalkyl groups. By way of example, where A is silicon and n=0, a disiloxane compound is formed, such as divinyltetramethyldisiloxane.

In the embodiment of the present invention where G is:

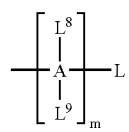

a structure is formed having a chain of single-bonded Group 14 atoms where the ends of the chain are capped by hydrocarbon fragments containing a double or triple bond. As with the previous embodiment, the substituent groups within the chain (i.e., $L^1$, $L^2$, $L^8$, $L^9$) may be either the hydrocarbon fragment with the double or triple bond or may be an inert alkyl, aryl, aralkyl or haloalkyl group. Where m=2, for example, a 3 atom chain is formed with 2 hydrocarbon fragment double or triple bond end groups and 6 $L^1$-$L^9$ substituent groups.

The reaction control agent is incorporated into the part to slow the ROMP mechanism upon mixing of the components, thereby increasing the working time of the resin before cure, and even to prevent completion of the ROMP mechanism in the absence of an elevated temperature above the mixing temperature. While numerous retarders are known for use with the platinum catalysts in the hydrosilation mechanism, unexpectedly, some of the most common of them are not effective with the ruthenium carbene catalysts in the ROMP mechanism. However, tetraallyl silane (TAS) and Tetraallyloxysilane (TAOS), for example, have been found to provide significantly increased working time, particularly with catalyst 4-2. Similarly, other compounds having a Group 14 central atom and one or more ligands having a hydrocarbon fragment and carbon-carbon double or triple bond have also been found to be effective, as explained further, below.

EXAMPLES

A procedure used for the preparation of UPE norbomenecarboxylates was as follows: 480.3 g 1,6 hexamethylene diisocyanate (HDI) were placed in a 5 L jacketed reactor under nitrogen atmosphere. The temperature was raised to 100° C. and 2.0 g of the catalyst dibutyl tin dilaurate were added. 3943.5 g of a polyether diol were added to the reaction mixture with an addition rate of ca. 100 mL/min under vigorous stirring. Stirring was continued for another 30 min and then 574.2 g of the HPNBC were added with an addition rate of ca. 30 mL/min. Stirring was continued for another 2 hours and then a sample was taken and titrated for the isocyanate value. If the isocyanate number was below 0.02 meq/g, then the reaction was stopped; otherwise, a small amount of HPNBC was added and the stirring was continued for 60 min.

Several analogs of UPE norbomenecarboxylates were prepared, as just described. Analytical data such as product viscosity, GPC, and HPNBC remaining as determined via a reverse phase HPLC assay are shown in Table 1. The Shore A hardness and the work time/set time properties when combined with the catalyst complex 3-1 are also shown. The standard testing procedures were as follows:

The standard procedure used for testing of resins with catalyst complex 3-1 was as follows: A 3.1 mg/g solution of catalyst complex 3-1 in dibenzyl toluene was prepared. The resin, 1 g, was mixed with 0.052 g of the catalyst solution in a sample vial by hand using a spatula until homogenous. The work time was defined as the time when the liquid does not flow easily from the spatula. After the work time was reached, the mass was tapped with the spatula. The set time was reached when the mass did not stick to the spatula anymore. The concentration of the catalyst in the final mixture was 160 ppm.

The standard procedure used for Shore A testing of resins with catalyst complex 4-2 was as follows: A 6.2 mg/g solution of catalyst complex 4-2 in dibenzyl toluene was prepared. A quantity of 2 g resin was mixed with 0.052 g of the catalyst solution in a sample vial by hand using a spatula until homogenous. Approximately 1 g of the resulting mixture was filled into a stainless steel mold of 10 mm diameter and 8 mm height and heat cured in a 120° C. oven for 1 hour. The Shore A hardness of the cured sample was measured after cooling. The concentration of the catalyst in the final mixture was 160 ppm.

The GPC samples were prepared at 20 mg/ml using tetrahydrofuran (THF) and 100 μl were injected onto the GPC, which consisted of a Waters 510 pump and a Waters 2414 RI detector. The columns (Waters Styragel HR3300×7.8 mm+Waters Styragel HR2 300×7.8 mm) and RI detector were both kept at 40° C. A THF mobile phase was used. The molecular weight (MW) of the resins was calculated using a calibration curve created from PEG standards.

TABLE 1

| Compound | MW PE[1] | Commercial Product | PE Type[2] | Viscosity [Pa * s] | MW by GPC | Shore A (4-2 Catalyst) | WT/ST [sec] (3-1 Catalyst) |
|---|---|---|---|---|---|---|---|
| 3a | 2000 | Bayer ACCLAIM ® 2200 | PO diol | 32.1 | 10500, 8400, 5800, 3100 | 59(1); 50(1)[3] | 115/240 |
| 3b | 3000 | Bayer ARCOL ® LG-56 | PO triol | 31.1 | 26300, 14100, 8700, 4300 | 35(1), brittle | 65/175 |
| 3c | 4000 | Bayer ACCLAIM ® 4200 | PO diol | 8.5 (30% CITROFLEX ® A4) | 13860, 9320, 4860 | 25(1) | 140/245 |
| 3d | 2800 | Bayer ARCOL ® E-351 | EO-PO, EO tipped | 18.3 | 10100, 7150, 3700 | 52(1); 53(1)[4] | 135/230 |
| 3e | 4000 | Bayer MULTRANOL ® 9111 | EO-PO, EO tipped | 6.2 (30% CITROFLEX ® A4) | 14400, 10500, 5630 | 28(1) | 125/250 |
| 3f | 1800 | NOF UNISAFE ™ DC-1800 | EO-THF, EO tipped | 5.1 (35% CITROFLEX ® A4) | 9225 | 45(1) | 105/210 |

[1]Weight Average Molecular Weight of Polyether
[2]PO = Propylene Oxide; EO = Ethylene Oxide
[3]Tetraallyloxysilane (TAOS) reaction control agent, 2000 ppm was used.

The UPE carboxylates reported in Table 1 were achieved with viscosities that can be easily handled and are convenient for mixing with catalysts to achieve elastomers after curing. Further, ROMP occurs unimpeded and the properties of hardness and work/set time are adequate for many applications. Also, the Shore A hardness values are within the same range as that for the acrylate analogs.

There are many potential uses for compositions of the present invention. By way of example and not limitation, dental applications may include: dental prostheses, tooth filling materials, crown and bridge materials, dental impression materials and orthodontic appliances. By way of example and not limitation, these materials can be used as adhesives or protective coatings for automotive, aerospace, architectural, and electric/electronic applications. The one-part compositions of the present invention may be particularly suitable for dental prostheses, orthodontic appliances such as orthodontic brackets that are optionally fiber reinforced, optical lenses, and electronic device packaging. The two-part compositions of the present invention may be particularly suitable for cements used in orthopedic surgery, such as for bone cementation and verterbroplasty procedures. All of the foregoing are intended to be exemplary uses for the compositions of the present invention and are not intended to limit the invention in any way.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention is therefore not limited to the specific details, representative apparatus and method and illustrative examples shown and described. Accordingly, departures may be made from such details without departing from the scope of the general inventive concept.

What is claimed is:

1. A composition comprising at least 0.1 wt. % of a substrate containing at least two cycloolefin groups capable of undergoing a metathesis reaction and a metal carbene complex catalyst capable of initiating the metathesis reaction, wherein the substrate is a urethane polyether carboxylate or a urethane polyester carboxylate, functionalized with at least two cycloolefin groups, and having the formula:

$$\left[ D-\overset{O}{\underset{\|}{C}}-O-Q_c \right]_d Z_a$$

wherein:
a=1-100, c=0 or 1 and d=2-100,

Q is a linear, branched, cyclic or polycyclic organic residue optionally containing siloxane groups (Si—O—Si) and optionally containing heteroatoms selected from the group consisting of B, N, O, Si, P, and S, Z is a linear, branched, cyclic or polycyclic urethane polyether or urethane polyester optionally containing siloxane groups (Si—O—Si) and optionally containing heteroatoms selected from the group consisting of B, N, O, Si, P, and S, and D is a cycloolefinic residue and is different than Q or Z; and wherein the catalyst has a structure selected from:

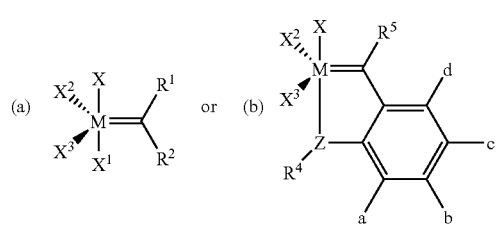

wherein:
M is ruthenium or osmium,

X is an alkylidene ligand with basicity higher than that of tricyclohexylphosphine ($PCy_3$), $X^1$ is either $PCy_3$ or a neutral electron donor ligand with basicity lower than that of $PCy_3$, $X^2$ and $X^3$ are either the same or different and are any anionic ligand, Z is oxygen (O) or sulfur (S), $R^1$ and $R^2$ are the same or different and are each a linear, branched, cyclic or polycyclic organic residue optionally containing siloxane groups (Si—O—Si) and optionally containing heteroatoms selected from the group consisting of B, N, O, Si, P, and S, and $R^4$, $R^5$, a, b, c, and d are the same or different and are each a linear, branched, cyclic or polycyclic organic residue optionally containing siloxane groups (Si—O—Si) and optionally containing heteroatoms selected from the group consisting of B, N, O, Si, P, and S.

2. The composition of claim 1 wherein the substrate comprises a dinorbornenyl dicarboxylate urethane polyester.

3. The composition of claim 1 wherein the substrate comprises a dinorbornenyl dicarboxylate urethane polyether.

4. The composition of claim 1 wherein D is a norbornenyl group; a=1, C=1, and Z is:

where R=hexyl and PE=polyether.

5. The composition of claim 1 wherein the substrate is a difunctional urethane polyether carboxylate and the polyether comprises one or more of butylene oxide units, ethylene oxide units or propylene oxide units, or combinations thereof.

6. The composition of claim 1 wherein D is a cycloolefinic residue selected from the group consisting of norbornenyl, norbornenylethyl, cyclopentenyl, 7-oxanorbornenyl, norbomadienyl, and 7-oxanorbomadienyl.

7. The composition of claim 1 wherein the catalyst has the structure:

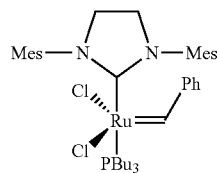

wherein Bu is butyl, Ph is phenyl and Mes is mesityl.

8. The composition of claim 1 further comprising a reaction control agent for slowing the progress of the metathesis reaction after mixing the substrate and the catalyst at a mixing temperature and having the structure:

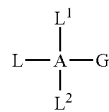

wherein:

G is selected from the group consisting of: $L^3$,

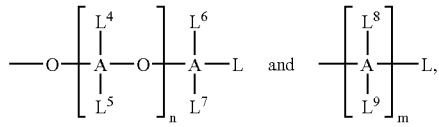

L is a hydrocarbon fragment containing a double or triple bond, $L^1$-$L^9$ are each independently selected from the group consisting of L, alkyl, aryl, aralkyl or haloalkyl, A is a Group 14 atom, and each of n and m 0-20.

9. The composition of claim 1 comprising a base part and a catalyst part, wherein the base part comprises the substrate, wherein the catalyst part comprises the metal carbene complex catalyst dissolved in a solvent that is miscible with the base part, and wherein the catalyst is capable of initiating the metathesis reaction upon mixing the base part with the catalyst part at room temperature.

10. A composition capable of undergoing a metathesis reaction upon mixing of its components, the components comprising:

a resin having an urethane polyester carboxylate backbone or an urethane polyether carboxylate backbone, functionalized with at least two cycloolefin groups capable of undergoing a metathesis reaction;

a ruthenium carbene complex catalyst capable of initiating the metathesis reaction in the composition, wherein the catalyst has the formula:

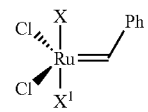

wherein Ph is phenyl, X is an alkylidene ligand having a basicity higher than that of tricyclohexyiphosphine ($PCy_3$), and $X^1$ is a phosphine, phosphite, phosphinite or phosphonite having a basicity lower than that of $PCy_3$; and a reaction control agent for preventing completion of the metathesis reaction after mixing the composition components at a mixing temperature and until exposing the composition to an elevated temperature above the mixing temperature, the reaction control agent having the structure:

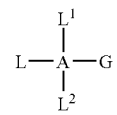

wherein:

G is selected from the group consisting of: $L^3$,

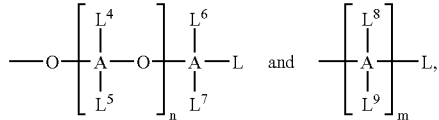

L is a hydrocarbon fragment containing an allyl group, a vinyl group, an ethynyl group or a propargyl group, $L^1$-$L^9$ are each independently selected from the group consisting of L, alkyl, aryl, aralkyl or haloalkyl, A is a Group 14 atom, n=0-20, and m=0-20.

11. The composition of claim 10 wherein the cycloolefin groups are selected from the group consisting of norbornenyl, norbornenylethyl, cyclopentenyl, 7-oxanorbornenyl, norbomadienyl, and 7-oxanorbomadienyl.

12. The composition of claim 10 wherein the catalyst has the structure:

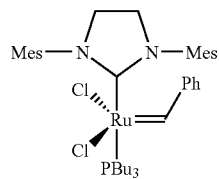

wherein Bu is butyl, Ph is phenyl and Mes is mesityl.

13. The composition of claim 10 wherein the reaction control agent is Tetraallyloxysilane.

14. The composition of claim 10 wherein the resin comprises a dinorbornenyl dicarboxylate urethane polyether.

15. The composition of claim 10 wherein the resin is:

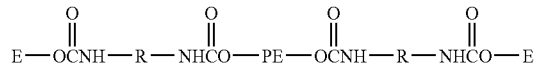

where R=hexyl, PE=polyether, and

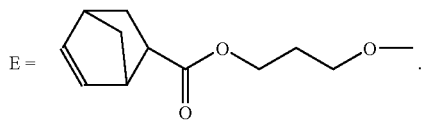

16. The composition of claim 9, wherein the catalyst has the structure (b).

17. The composition of claim 16 wherein the cycloolefin groups are selected from the group consisting of norbornenyl, norbornenylethyl, cyclopentenyl, 7-oxanorbornenyl, norbornadienyl, and 7-oxanorbornadienyl.

18. The composition of claim 16 wherein M is ruthenium; X is 1,3-bis (2,4,6-trimethylphenyl)-imidazol-2-ylidene; $X^2$ and $X^3$ are chlorine atoms; Z is oxygen; $R^4$ is 2-propyl; a, b, c and d are each either hydrogen or methoxy; and $R^5$ is hydrogen.

19. The composition of claim 16 wherein the resin comprises a dinorbornenyl dicarboxylate urethane polyether.

20. The composition of claim 16 wherein the base resin is:

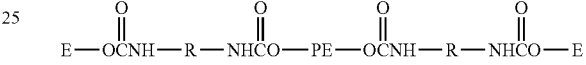

where R=hexyl, PE=polyether, and

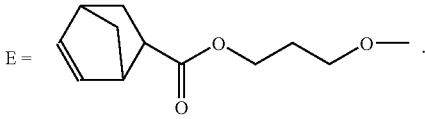

* * * * *

UNITED STATES PATENT AND TRADEMARK OFFICE
CERTIFICATE OF CORRECTION

PATENT NO. : 7,645,443 B2  Page 1 of 1
APPLICATION NO. : 11/276270
DATED : January 12, 2010
INVENTOR(S) : Angeletakis It is certified that error appears in the above-identified patent and that said Letters Patent is hereby corrected as shown below:

Title Page, should read (*) Notice: Subject to any disclaimers, term of this patent is extended or adjusted under 35 U.S.C. 154(b) by 929 days.

Col. 18, line 14, Claim 8, "each of n and m 0-20." should read --each of n and m = 0-20.--.

Signed and Sealed this

Third Day of August, 2010

David J. Kappos
*Director of the United States Patent and Trademark Office*